United States Patent
Engelhardt et al.

(10) Patent No.: US 11,992,268 B2
(45) Date of Patent: May 28, 2024

(54) METHOD FOR DETERMINING A STEREOTACTIC BRAIN TARGET

(71) Applicants: UNIVERSITE DE BORDEAUX, Bordeaux (FR); INSTITUT POLYTECHNIQUE DE BORDEAUX, Talence (FR); CENTRE HOSPITALIER UNIVERSITAIRE DE BORDEAUX, Talence (FR); CENTRE NATIONAL DE LA RECHERCHE SCIENTIFIQUE, Paris (FR); INSTITUT NATIONAL DE RECHERCHE EN INFORMATIQUE ET EN AUTOMATIQUE (INRIA), Le Chesnay (FR)

(72) Inventors: Julien Engelhardt, Villenave d'Ornon (FR); Nejib Zemzemi, Bordeaux (FR); Emmanuel Cuny, Bordeaux (FR)

(73) Assignees: UNIVERSITE DE BORDEAUX, Bordeaux (FR); INSTITUT POLYTECHNIQUE DE BORDEAUX, Talence (FR); CENTRE HOSPITALIER UNIVERSITAIRE DE BORDEAUX, Talence (FR); CENTRE NATIONAL DE LA RECHERCHE SCIENTIFIQUE, Paris (FR); INSTITUT NATIONAL DE RECHERCHE EN INFORMATIQUE ET EN AUTOMATIQUE (INRIA), Le Chesnay (FR)

( * ) Notice: Subject to any disclaimer, the term of this patent is extended or adjusted under 35 U.S.C. 154(b) by 498 days.

(21) Appl. No.: 17/293,433

(22) PCT Filed: Nov. 18, 2019

(86) PCT No.: PCT/EP2019/081571
§ 371 (c)(1),
(2) Date: May 12, 2021

(87) PCT Pub. No.: WO2020/099671
PCT Pub. Date: May 22, 2020

(65) Prior Publication Data
US 2021/0401504 A1 Dec. 30, 2021

(30) Foreign Application Priority Data
Nov. 16, 2018 (FR) ..................... 1860588

(51) Int. Cl.
*A61B 34/10* (2016.01)
*G06N 20/10* (2019.01)
(Continued)

(52) U.S. Cl.
CPC ............ *A61B 34/10* (2016.02); *G06N 20/10* (2019.01); *G16H 20/40* (2018.01); *G16H 50/70* (2018.01); *A61B 2034/107* (2016.02)

(58) Field of Classification Search
None
See application file for complete search history.

(56) References Cited

U.S. PATENT DOCUMENTS

| 2014/0171791 | A1  | 6/2014 | Simon et al. |
| 2020/0098477 | A1* | 3/2020 | Peták .................... G16H 50/70 |
| 2023/0289571 | A1* | 9/2023 | Pauletto ................ G06N 3/088 |
| | | | 706/16 |

FOREIGN PATENT DOCUMENTS

WO 2018/008034 A2 1/2018

OTHER PUBLICATIONS

Kim, et al., "Automatic localization of the subthalamic nucleus on patient-specific clinical MRI by incorporating 7T MRI and machine learning: Application in deep brain stimulation", Hum Brain Mapp., vol. 40, No. 2, 2019.

* cited by examiner

*Primary Examiner* — Dov Popovici
(74) *Attorney, Agent, or Firm* — BakerHostetler (57) ABSTRACT

A method for determining a stereotactic brain target includes at least one target point, the method comprising the following steps: selecting patients for whom the result measured

(Continued)

following treatment at at least one target point is greater than or equal to a threshold, postoperative imaging having been performed for each of the patients; processing the postoperative imaging so as to determine coordinates of the at least one target point; selecting brain marker points; processing the postoperative imaging so as to determine coordinates of the marker points; creating a learning database comprising the coordinates of the target points and the coordinates of the marker points determined for all of the selected patients; determining a prediction function giving the coordinates of at least one target point according to the coordinates of the marker points by using the learning database and a supervised statistical learning method; processing preoperative imaging of a new patient to be treated so as to determine coordinates of the marker points of the new patient; using the prediction function so as to obtain the coordinates of at least one target point for the new patient according to the coordinates of the marker points determined for the new patient.

14 Claims, 4 Drawing Sheets

(51) Int. Cl.
*G16H 20/40* (2018.01)
*G16H 50/70* (2018.01)

METHOD FOR DETERMINING A STEREOTACTIC BRAIN TARGET

CROSS-REFERENCE TO RELATED APPLICATIONS

This application is a National Stage of International patent application PCT/EP2019/081571, filed on Nov. 18, 2019, which claims priority to foreign French patent application No. FR 1860588, filed on Nov. 16, 2018, the disclosures of which are incorporated by reference in their entirety.

FIELD OF THE INVENTION

Technical Field of the Invention

The field of the invention is that of neurosurgery, and it relates more specifically to a method for preparation before a neurosurgical intervention.

The invention relates more particularly to a method for precisely determining a stereotactic brain target.

The invention may relate in particular to a method for determining a brain target to be stimulated as a preparation step before the implantation of an electrode for deep brain stimulation.

Background

Determining a brain target is essential in any neurosurgical treatment protocol, in particular in stereotaxis. Stereotaxis is a neurosurgical technique that uses a method for three-dimensionally identifying intracranial structures assisted by medical imaging in order to precisely determine, on the basis of a point located inside the brain, the volume and location of a region of the brain or of a lesion in which the neurosurgeon has to intervene.

One intervention may be deep brain stimulation (DBS). Deep brain stimulation is a very effective surgical technique for relieving patients with neurological pathologies such as Parkinson's disease, essential tremor disease, dystonia, obsessive-compulsive disorder, Tourette's syndrome, refractory epilepsy or even severe and treatment-resistant depression.

Deep brain stimulation consists in stimulating an overactive structure deep in the brain. The stimulation may inhibit or activate neurons, the goal being to modify the functioning of neural networks. It may reduce or even eliminate symptoms and improve the quality of life of patients resistant to usual treatment.

Deep brain stimulation is generally performed by implanting electrodes into a brain structure that corresponds to a nucleus, and in general usually a portion of a nucleus in the gray matter (neural cell bodies). Throughout the rest of the present description, the term "nucleus" may refer either to a nucleus or to a portion of a nucleus.

The electrodes receive an electric current of low intensity which is thus delivered to the target nucleus.

The brain structures targeted in deep brain stimulation vary depending on the pathologies to be treated: the subthalamic nucleus (STN) to treat Parkinson's disease, the ventral intermediate nucleus of the thalamus (VIM) to treat essential tremor, the internal globus pallidus (GPi) to treat dystonia and some forms of Parkinson's disease. The dimensions of these nuclei do not exceed a few millimeters apart from the internal globus pallidus.

Among the challenges presented by this technique are identifying (i.e. defining and/or locating) the nucleus to be stimulated, marking (i.e. targeting) the identified nucleus and positioning the stimulation electrodes.

The first challenge concerns identifying the nucleus to be stimulated. For example, with regard to the VIM, there are a number of nomenclatures for the human thalamus, resulting in disagreement over the identification of the VIM. Problems with anatomical definition are less substantial for the STN than for the VIM. Disagreement remains, however, as to which sub-portion of the STN should be stimulated, or even whether the fibers above the STN ("zona incerta") are not actually the best target.

Even if this identification problem were solved, there are still the other challenges of locating the identified nucleus and therefore positioning the stimulation electrodes. For example, while the GPi nucleus for treating dystonia can be located using magnetic resonance imaging (MRI), the STN nucleus and the VIM nucleus are much more difficult or even impossible to locate using MRI that can be used in current stereotactic practice (typically MRI with a magnetic field at 1.5 or 3 teslas). Thus, while the locating of certain nuclei has certainly improved by virtue of progress in MRI—for example, a combination of MRI sequences makes it possible to visualize the STN nucleus (3D T1, T2, SWI ("susceptibility weighted imaging"), FGATIR ("fast gray matter acquisition inversion recovery"), FLAIR ("fluid attenuation inversion recovery") sequences)—it has been demonstrated that the STN nucleus visualized radiologically by MRI does not correspond exactly to the STN nucleus for which stimulation works (which may be measured using the intraoperative electrophysiological recording technique described later), with errors of more than 5 mm being able to be seen on the individual level.

For these less visible or non-locatable areas, it is known practice to implement what are called "indirect" locating techniques based on stereotactic atlases. The principle of these indirect locating techniques is to have a Cartesian reference frame comprising anatomical marker points that can easily be identified by MRI, and an atlas giving the location of various brain areas (e.g. various brain nuclei), not all of which can be identified by MRI. The principle is to locate the position of any area in the brain of any individual on the basis of all or some of the marker points using this atlas. A set of functions of proportionality between the marker points and the points in the atlas is used, thus making it possible to realign any brain, regardless of its size or its anatomical specificities.

Stereotactic atlases are used more widely when the brain is studied, well beyond application to DBS. One known example is the Talairach atlas or coordinates. The center of this reference frame (i.e. the point with coordinates x=0, y=0, z=0) is the superior and posterior edge of the anterior commissure in the mid-sagittal plane (i.e. the plane parallel to the internal face of the brain also called the interhemispheric plane); this point, called the "CA" (also called the "AC"), is very easy to see in MRI. Another reference point is used: the inferior and anterior edge of the posterior commissure (still in the mid-sagittal plane); this point, called the "CP" (also called the "PC") is also very easy to see in MRI. The three axes of the coordinate system are then defined as follows: the Oy axis passes through CA and CP and is oriented toward the front of the skull. The Oz axis is the axis of the sagittal plane perpendicular to Oy and passing through CA. It is oriented toward the top of the skull. Lastly, the Ox axis is the axis orthogonal to Oy and to Oz passing through CA; it is oriented from left to right. Another example is the Schaltenbrand atlas which has made it possible to simplify the Talairach system by taking the midpoint of the segment [CACP], called the mid-commissural point, as the center of the stereotactic reference frame. The points CA and CP represent, respectively, the anatomical center of the anterior and posterior commissures.

Once the nucleus to be stimulated has been identified according to the pathology to be treated, it is located in the atlas used using marker points that can be identified by MRI. In deep stimulation, the stimulation electrode should be positioned in the nucleus indirectly identified in this way.

The problem with the known indirect locating techniques is that they are based on the assumption of proportionality of the brain, as if the variability in the distance between two points could account for all observed anatomical variabilities, which is not the case. This therefore necessarily leads to targeting inaccuracies which may be highly detrimental in deep brain stimulation.

To remedy these targeting inaccuracies, current surgery cannot be done without electrophysiological recordings and intraoperative clinical tests in order to ensure that the electrode is correctly positioned in the target. The principle of intraoperative electrophysiological recording is to implant parallel microelectrodes in the region that is presumed to contain the anatomical target, in order to stimulate the neurons in the region and to record the effect of the stimulation intraoperatively. This technique makes it possible to optimize the definitive position of the electrode and thus refine targeting. While this technique improves targeting accuracy, it is nevertheless very lengthy (operating time of the order of 7 to 10 hours) and it entails a risk of infection, and an increase in the risk of hemorrhage proportional to the number of recording microelectrodes used. In addition, the definitive implantation of the electrode is not always easy to achieve precisely. Lastly, the surgical operation requires the participation of the patient in order to be able to test the clinical effect of the stimulation and thus optimize the position of the electrode. It therefore has to be performed under local anesthesia, which is very uncomfortable for the patient.

The aforementioned techniques are based on an approach consisting in defining a nucleus to be stimulated, then in targeting said nucleus, and then in positioning a stimulation electrode in the case of DBS. Analysis of the obtained result may lead to the position of the stimulation electrode and/or the location of the anatomical target in the reference frame used (generally the Schaltenbrand or Talairach reference frame) being moved.

Another technique consists of an indirect approach consisting in identifying patients for whom deep brain stimulation has been successful, identifying the position of the electrodes in these patients and correlating it with reference points that are easily identifiable in MRI, and then applying this to new patients to be treated using the reference points. This approach makes it possible to avoid compounding the inaccuracy factors which are identifying the nucleus to be stimulated, locating (targeting) the target and positioning the stimulation electrodes in the target. In this case, reference is made to a "clinical target" or to a "functional target", given that the stimulation target is determined on the basis of clinical cases which have worked.

Such an approach is described in the thesis document by François Caire "Intraoperative imaging of deep brain stimulation electrodes and proposal of a new method for indirect stereotactic location of the subthalamic target" [translation of original title "Imagerie per-opératoire des électrodes de stimulation cérébrate profonde et proposition d'une nouvelle modalité de repérage stéréotaxique indirect de la cible subthalamique"]. The solution proposed in this thesis includes the following steps:

selecting patients with a very good response to subthalamic deep stimulation;
retrieving postoperative MRIs of said patients;
constructing, for each postoperative MRI, the standard CACP stereotactic space: for this, the points CA and CP and the interhemispheric plane are identified;
determining, in postoperative MRIs, the coordinates of the active simulation contact;
determining, in postoperative MRIs, various anatomical marker points; calculating the correlation between each coordinate of the active contact and the corresponding coordinate of each marker point, using a linear regression model;
when the correlation is correct, calculating the equation of the regression line on the basis of the marker points that provide the best correlation with the x, y and z coordinates of the active contacts; calculating the coordinates of a theoretical target using this equation; comparing the coordinates of this theoretical target with the actual coordinates of the active contacts.

The drawback of this method is that it assumes the variability (or the homothety) of the brain on only three axes, while remaining in a proportionality system (here a linear regression method). This is better than assuming that the variability of the distance between two points (CA and CP) can account for all observed anatomical variabilities, but it is nevertheless still insufficient. Thus, the mean error in the method is 2.5±0.6 mm, which is quite large with respect to the size of the structures to be targeted.

SUMMARY OF THE INVENTION

The invention aims to overcome the aforementioned drawbacks of the prior art.

More particularly, the invention aims to provide a method for determining a stereotactic brain target which allows better targeting accuracy, and which is easy to use. It aims to provide a method for determining a stereotactic brain target used as a preparation step before a neurosurgical treatment which allows the effectiveness of such a treatment to be improved.

One subject of the invention allowing this objective to be achieved is a method for determining a stereotactic brain target comprising at least one target point, said method comprising the following steps:

selecting patients for whom the result measured following treatment at at least one target point is greater than or equal to a threshold, postoperative imaging having been performed for each of said patients; processing said postoperative imaging so as to determine, for each selected patient, all or some of the coordinates of the at least one target point;
selecting brain marker points;
processing said postoperative imaging so as to determine, for each selected patient, all or some of the coordinates of the selected marker points;
creating a learning database comprising the coordinates of the target points and the coordinates of the marker points determined for all of the selected patients;
determining a prediction function giving the coordinates of at least one target point according to the coordinates of the marker points by using the learning database and a supervised statistical learning method; processing preoperative imaging of a new patient so as to determine all or some of the coordinates of the marker points of said new patient; using the prediction function so as to obtain the coordinates of at least one target point for said new patient according to the coordinates of the marker points determined for said new patient.

Preferably, the invention relates to a method for determining a stereotactic brain target comprising at least one target point, said method being implemented prior to neurosurgical treatment at said target for a given pathology and comprising the following steps:
- selecting a plurality of clinical cases of patients for whom the result measured following the treatment performed for said pathology at at least one target point is greater than or equal to a threshold, postoperative imaging having been performed for each of said patients;
- selecting a mathematical coordinate system, preferably an orthonormal Cartesian coordinate system;
- processing said postoperative imaging so as to determine, for each selected clinical case, all or some of the coordinates of the at least one target point in the selected coordinate system;
- selecting a plurality of brain marker points;
- processing said postoperative imaging so as to determine, for each selected clinical case, all or some of the coordinates of the brain marker points;
- creating a learning database comprising the determined coordinates of the target points and the determined coordinates of the marker points of all of the selected clinical cases;
- determining a prediction function giving the coordinates of at least one target point according to the marker points by using the learning database and a supervised statistical learning method;
- processing preoperative imaging of a new patient to be treated for said pathology so as to determine all or some of the coordinates of the marker points of said new patient;
- using the prediction function so as to obtain the coordinates of at least one target point for said new patient according to the coordinates of the marker points determined for said new patient.

According to the invention, the marker points are characteristic points of anatomical structures in the brain that can be located in a given mathematical coordinate system, and are anatomical points that are visible, in particular, using conventional imaging.

According to the invention, the target points are points to which the neurosurgical treatment has been applied for the clinical cases, or has to be applied for the new patients.

The method according to the invention is based on data from clinical cases of patients for whom the efficacy of the treatment has been determined. Thus, the target points on which the learning is carried out are clinically validated targets. This makes it possible to improve the neurosurgical treatment which may follow the method according to the invention.

To do this, the method according to the invention is based on postoperative imaging available for these patients, which imaging is processed in order to deduce therefrom: the points to which the treatment was applied (target points) and marker points chosen from among characteristic points of anatomical structures in the brain that are visible, in particular, using conventional imaging. The coordinates of these target points and these marker points are integrated into a learning database which makes it possible to determine a prediction function. The prediction function makes it possible to give at least one target point as a function of marker points. The prediction function is constructed from the learning database using a supervised statistical learning method.

The method according to the invention may be based on imaging extracted from conventionally used MRI, for example 1.5 T MRI. It is not necessary to use more powerful MRI, for example 3 T or 7 T MRI, which is much more expensive (especially in terms of hardware), and which requires higher radiology skills than 1.5 T MRI. These images are processed in order to determine the coordinates of the marker points.

The method according to the invention seeks to control brain variability in a multidimensional manner rather than on one, two or three axes. By opting for a supervised statistical learning technique, the method makes it possible to overcome this brain variability, and it thus allows better targeting accuracy.

In addition, the target points are determined as clinically validated targets, unlike other methods where it is first sought to identify and then to locate the brain structure to be stimulated (STN, VIM, etc.), and then to implant the stimulation electrode in the brain structure identified and located in this way. Thus, this makes it possible to avoid compounding the inaccuracy factors and therefore to improve targeting accuracy.

In this sense, the method according to the invention does not seek to construct an anatomical atlas in order to visualize brain structures (STN, VIM, etc.) as a function of marker points, but rather it seeks target points in order to know directly where to apply the treatment and does so by using target points that have worked for patients. Indeed, the inventors have identified that, even if the center of the anatomical structure (STN, VIM, etc.) is located, nothing guarantees that this center is the correct target to be stimulated, as explained above.

The method according to the invention further makes it possible to determine a target (a plurality of points) and not just one point, and thus to construct a target in 3D.

Once the target has been determined for a new patient, it is possible to mark the position of the target in the MRI with a sign, for example a cross. To mark with a cross, it is possible to change the value of five pixels in each of the three directions of the mathematical coordinate system by assigning the maximum value (which corresponds to the color white) to these pixels. This makes it possible to form a white cross, the center of this white cross allowing the practitioner to visualize the target.

Lastly, the method for determining a stereotactic target according to the invention may be used as a decision aid, in particular in preparation for any neurosurgical treatment requiring at least one precise brain target to be determined.

In particular, in the case of deep brain stimulation, the method of the invention makes it possible to dispense with the electrophysiology which is generally used to ensure that the electrode is correctly positioned in the brain structure to be stimulated. Therefore, the method of the present invention is not invasive for the patient.

By using suitable techniques for selecting and optimizing the parameters of the prediction function (also called the "metamodel"), the method allows targeting accuracy to be further improved.

Thus, according to one advantageous embodiment, the method may further comprise a step of:
- consolidating the prediction function using a cross-validation method, said consolidating step resulting in a consolidated prediction function giving the coordinates of at least one target point according to the marker points;

the step of using the prediction function consisting in using the consolidated prediction function.

According to one embodiment, the imaging processed to determine the coordinates of the marker points and of the at least one target point is at least one MRI image, preferably a plurality of MRI images.

The method may thus comprise a step of performing postoperative MRI in the selected patients and the determination of the marker points may comprise a step of processing the images obtained by MRI and/or the determination of the at least one target point may also comprise a step of processing the images obtained by MRI.

The method may alternatively or additionally comprise a step of performing a postoperative computed tomography (CT) scan in the selected patients and the determination of the at least one target point may comprise a step of processing the images obtained by CT and/or the determination of the marker points may comprise a step of processing the images obtained by CT.

According to one embodiment, the supervised statistical learning method comprises the use of a kernel ridge regression method in a reproducing kernel Hilbert space.

According to another embodiment, the supervised statistical learning method comprises the use of a method of support-vector machine type.

According to another embodiment, the supervised statistical learning method comprises the use of a method of neural network type.

According to one embodiment, the cross-validation method comprises the use of a "leave-one-out cross-validation" method.

According to another embodiment, the cross-validation method comprises the use of a "leave-k-out cross-validation" method.

According to one particular embodiment, the chosen mathematical coordinate system is an orthonormal Cartesian coordinate system, the straight line passing through the superior and posterior edge of the anterior commissure and the inferior and anterior edge of the posterior commissure forming the Oy axis, the inferior and anterior edge of the posterior commissure forming the center of the coordinate system, and the Oz axis being the straight line perpendicular to the Oy axis in the interhemispheric plane.

According to one particular embodiment, the marker points are chosen from among the following eighteen points, preferably defined with respect to the mathematical coordinate system chosen previously:

the first marker point being the mamillothalamic fasciculus on the third axial plane;

the second, third and fourth marker points being the anterior point of the putamen on each of the first, second and third axial planes;

the fifth and sixth marker points being the medial point of the putamen on the first and second axial planes;

the seventh and eighth marker points being the posterior point of the putamen on the first and second axial planes;

the ninth marker point being the habenular commissure on the second axial plane;

the tenth marker point being the anterior edge of the thalamus on the second axial plane;

the eleventh marker point being the posterior edge of the thalamus on the second axial plane;

the twelfth marker point being the anterior commissure;

the thirteenth marker point being the medial edge of the third ventricle at the mid-commissural point;

the fourteenth marker point being the height of the thalamus on the sagittal plane passing through the thirteenth marker point;

the fifteenth marker point being the midpoint of the segment defined by the thirteenth and fourteenth marker points;

the sixteenth marker point being the anterior edge of the thalamus on the straight line parallel to the straight line passing through the superior and posterior edge of the anterior commissure and the inferior and anterior edge of the posterior commissure and passing through the fifteenth marker point;

the seventeenth marker point being the superior edge of the putamen on the coronal plane passing through the fifth marker point; and the eighteenth marker point being the lateral edge of the putamen on the coronal plane passing through the fifth marker point.

According to one embodiment, all of these eighteen marker points are used.

Other marker points may be used.

Other mathematical coordinate systems, in particular the coordinate systems commonly used in known stereotactic atlases, may be used.

According to one embodiment, the method comprises an additional step of adding functional data to the learning database, said functional data being able to add at least one indicator of the degree of confidence in the target points and the marker points of the clinical cases.

According to one embodiment, the method is implemented prior to deep brain stimulation. According to another embodiment, the method is implemented prior to Gamma Knife. According to another embodiment, the method is implemented prior to focused ultrasound treatment.

The marker points, or the target points, are adapted according to the planned treatment, and therefore according to the pathology to be treated.

A second subject of the invention is a data processing system comprising a processor configured to implement all or some of the steps of the method. It may be a computer, a tablet, a smartphone, etc.

A third subject of the invention is a computer program comprising instructions which, when the program is executed by a processor, cause it to implement all or some of the steps of the method.

BRIEF DESCRIPTION OF THE DRAWINGS

Other features and advantages of the invention will become apparent through the following description given by way of non-limiting illustration, provided with reference to the appended figures, in which.

DETAILED DESCRIPTION

The invention consists in determining target points for neurosurgical treatment, which target points are generally positioned in deep intracerebral structures that are not visible by conventional imaging.

For this, the invention consists in using marker points that are visible by conventional imaging and a prediction function. Said prediction function is constructed using a learning database comprising marker points and target points originating from clinical cases of patients for whom the efficacy of the treatment has been observed. Efficacy is determined by at least one measured result as explained further below. A supervised statistical learning technique is used to construct said prediction function (or metamodel), which is thus able to provide the coordinates of at least one target point as a function of marker points.

The description of the embodiments which follows is generally illustrated in the case where the method according to the invention is implemented as preparation for a treatment by deep brain stimulation, it being understood that the invention, and in particular said embodiments, may be implemented more generally as preparation for any neurosurgical treatment requiring at least one precise brain target to be determined.

In the particular application to deep brain stimulation, a target point may also be referred to as a stimulation point.
Selecting the Clinical Cases (Patients):

Patients for whom electrode stimulation at at least one stimulation point has been effective in treating the same pathology are selected. Efficiency is determined by at least one measured result.

The pathology may be Parkinson's disease, essential tremor disease, dystonia, obsessive-compulsive disorder, Tourette's syndrome, refractory epilepsy, or even severe and treatment-resistant depression.

The target structure for stimulation may be the subthalamic nucleus (STN) to treat Parkinson's disease, the ventral intermediate nucleus of the thalamus (VIM) to treat essential tremor, the internal globus pallidus (GPi) to treat dystonia and some forms of Parkinson's disease.

This result measured following the neurosurgical treatment may be a postoperative clinical evaluation, an evaluation by anatomical or radiological localization, or an electrophysiological evaluation.

A postoperative clinical evaluation is performed using scales specific to the pathology being treated and/or quality-of-life scales, for example three months after treatment. This makes it possible to determine a first criterion and therefore a first threshold for the selection of clinical cases (patients).

An evaluation by anatomical or radiological localization is defined by anatomical or radiological preoperative targeting and a distance between said preoperative targeting and the postoperative treatment point (for example the position of the electrode in the case of DBS). This makes it possible to determine a second criterion and therefore a second threshold for the selection of clinical cases (patients).

An electrophysiological evaluation is defined by intraoperative identification of the target and the distance between said intraoperative identification and the postoperative treatment point (for example the position of the electrode in the case of DBS). This makes it possible to determine a third criterion and therefore a third threshold for the selection of clinical cases (patients).

The various evaluation criteria may be combined in order to define a combined threshold value.

The selected patients will make it possible to build a statistical learning database comprising pairs of marker points/target points for at least one pathology.

In addition, the method may comprise a step of adding functional data to the learning database of patients. These data may comprise the parameters for evaluating the symptoms of the pathology preoperatively and the degree of improvement of the symptoms of the pathology postoperatively. By way of example, the UPDRS scale (Unified Parkinson's Disease Rating Scale) for Parkinson's disease or the Fahn-Tolosa-Marin scale for essential tremor may be used.

In addition, in the case of deep brain stimulation, these data may comprise the electrical parameters (amplitude, frequencies and durations) of the stimulation.

All of these functional data may thus be entered into the learning database and into the metamodel, in addition to the target points and marker points. All or some of these functional data may be used in a cost function as at least one indicator of confidence in the patient data. In this case, these data are translated mathematically in the metamodel as weight functions which will weight the cost function to be minimized.

The marker points are characteristic points of anatomical structures in the brain that can be located in the mathematical coordinate system used, and are anatomical points that are visible using conventional imaging, in particular MRI.

Thus, the marker points may be obtained by using imaging originating from existing postoperative MRI.

Figure 1:
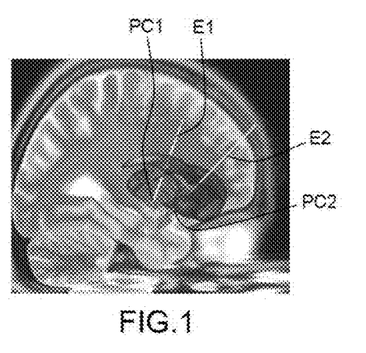
FIG. 1 is a synthetic image illustrating the implantation of two stimulation electrodes at two different points and in two different directions.
Figure 2:
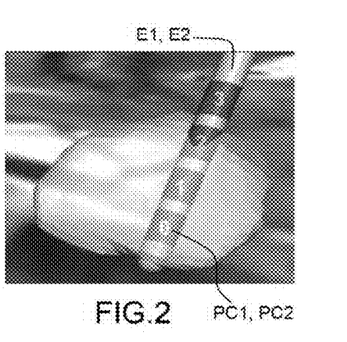
FIG. 2 is a synthetic image illustrating an electrode implanted in a target and comprising a plurality of active contacts.

In the particular embodiment described, a target point (or stimulation point) is a point of implantation of the electrode. A stimulation point is characterized by its coordinates in the mathematical coordinate system used. It may also be characterized by the direction of an electrode (E1, E2) implanted at this point (PC1, PC2), as illustrated in FIGS. 1 and 2.

Each stimulation point is determined, for example, by carrying out and using postoperative imaging, for example by MRI or by computed tomography ("CT") and by reconstructing the electrode in the reference frame on the basis of the distal artefact and the artefacts created by the various contacts.

In the present description, a target point or the set of target points constitutes a "target", or "stimulation target" in the particular application of deep brain stimulation. A target is characterized by the coordinates of each target point. In the particular application of deep brain stimulation, it may further be characterized by the direction of the electrode at a stimulation point (coordinates of the direction vector of the electrode).

These marker and target points determined for the selected patients thus constitute a statistical learning database, which may be enriched with other data.

The method according to the invention comprises the use of a regression method based on supervised statistical learning, using said learning database, so as to establish a prediction function between the marker points and the one or more target points.

The following description, given in particular with reference to FIGS. 3A to 3F and 4A to 4D, describes one particular embodiment of the method.

Step of Constructing and/or Initializing the Learning Database

Mathematical Coordinate System Used

"CA" denotes the upper and posterior edge of the anterior commissure and "CP" denotes the lower and anterior edge of the posterior commissure.

Figure 4A:
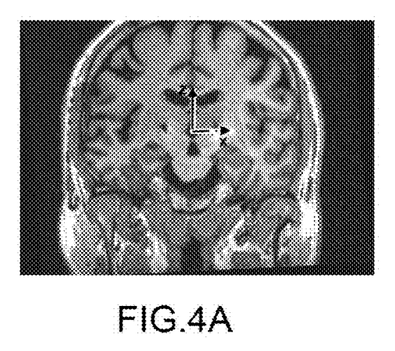
FIGS. 4A and 4C are three MRI images illustrating the axes of the mathematical coordinate system CA-CP and FIG. 4D shows the mathematical coordinate system CA-CP in 3D.
Figure 4B:
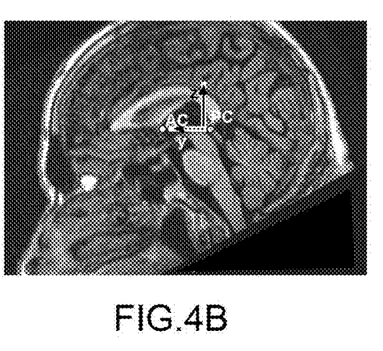
Figure 4C:
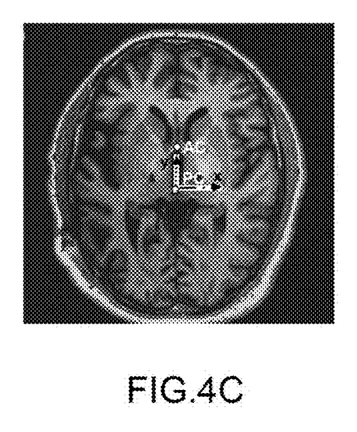
Figure 4D:
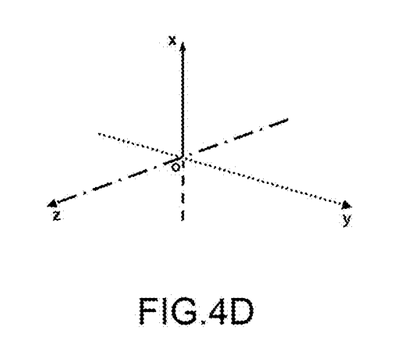

The mathematical coordinate system used is illustrated in FIGS. 4A to 4D. FIG. 4A is a coronal section, FIG. 4B is a mid-sagittal section and FIG. 4C is an axial section. FIG. 4D is a 3D view illustrating the three axes.

The illustrated coordinate system is an orthonormal Cartesian coordinate system having as its origin the point CP and the Oy axis of which is the straight line passing through the points CA and CP (symbolized "CACP"). The Oz axis is the straight line perpendicular to the line (CACP) in the interhemispheric plane and the Ox axis is deduced. Such a coordinate system is symbolized in the present description by CA-CP.

Usable Marker Points

In one exemplary embodiment, the usable marker points number 18 (m=18) corresponding to the points shown in particular in FIGS. 3A to 3F. The eighteen usable marker points are:

first marker point (FMT): the mamillothalamic fasciculus on the third axial plane;
second, third and fourth marker points (PA1, PA2, PA3): the anterior point of the putamen on each of the first, second and third axial planes;
fifth and sixth marker points (PM1, PM2): the medial point of the putamen on the first and second axial planes;
seventh and eighth marker points (PP1, PP2): the posterior point of the putamen on the first and second axial planes;
ninth marker point (CH): the habenular commissure on the second axial plane;
tenth marker point (BAT): the anterior edge of the thalamus on the second axial plane;
eleventh marker point (BPT): the posterior edge of the thalamus on the second axial plane;
twelfth marker point (CA): the anterior commissure;
thirteenth marker point (A): the medial edge of the third ventricle at the mid-commissural point called the "MCP" point;
fourteenth marker point (B): the height of the thalamus on the sagittal plane passing through the thirteenth marker point (A);
fifteenth marker point (C): the midpoint of the segment [AB] defined by the thirteenth and fourteenth marker points;
sixteenth marker point (D): the anterior edge of the thalamus on the straight line parallel to (CACP) and passing through the fifteenth marker point (C);
seventeenth marker point ($P_{culm}$): the superior edge of the putamen on the coronal plane passing through the fifth marker point (PM1), and eighteenth marker point ($P_{lat}$): the lateral edge of the putamen on the coronal plane passing through the fifth marker point (PM1).

The axial reference plane (or transverse plane) is the plane passing through the center of the CA-CP coordinate system and the Ox and Oy axes. The first, second and third axial planes are defined in relation to the axial reference plane.

The first axial plane corresponds to the plane parallel to the axial reference plane passing through the z(C)-5 mm coordinate (point located 5 mm below the z coordinate of the fifteenth marker point and the x and y coordinates of which are equal to zero).

The second axial plane corresponds to the plane parallel to the axial reference plane passing through the z(C) coordinate (z coordinate of the fifteenth marker point and the x and y coordinates of which are zero).

The third axial plane corresponds to the plane parallel to the axial reference plane passing through the z(C)-10 mm coordinate (10 mm below the z coordinate of the fifteenth marker point and the x and y coordinates of which are zero).

What should be understood by sagittal plane is any plane coincident with or parallel to the plane formed by the Oy and Oz axes. Furthermore, the sagittal plane chosen in the embodiment passes through the x coordinate of the thirteenth marker point (A).

What should be understood by coronal plane is any plane coincident with or parallel to the plane formed by the Ox and Oz axes. Furthermore, the coronal plane chosen in the embodiment passes through the y coordinate of the fifth marker point (PM1).

Figure 3A:
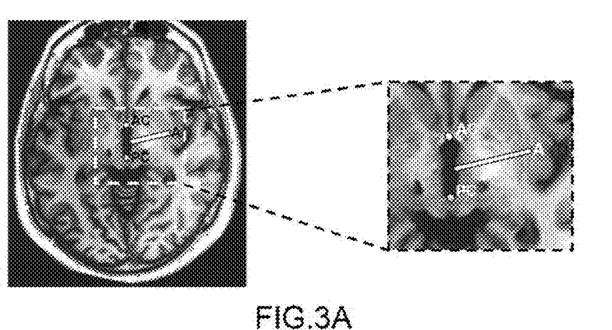
FIGS. 3A to 3F are MRI images viewed along various sections illustrating 18 marker points.
Figure 3B:
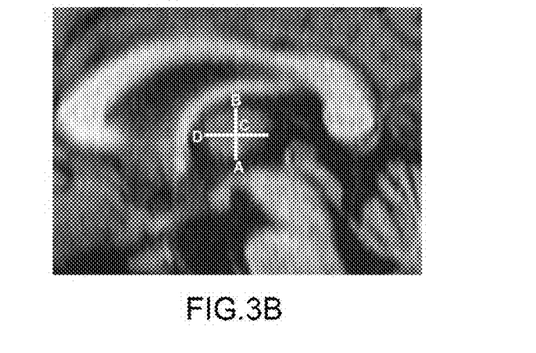
Figure 3C:
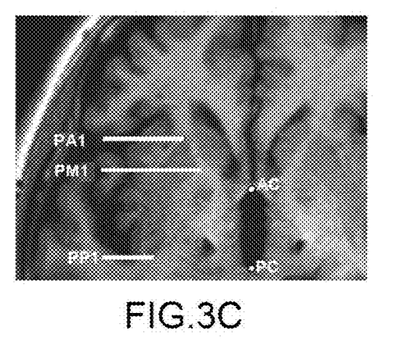
Figure 3D:
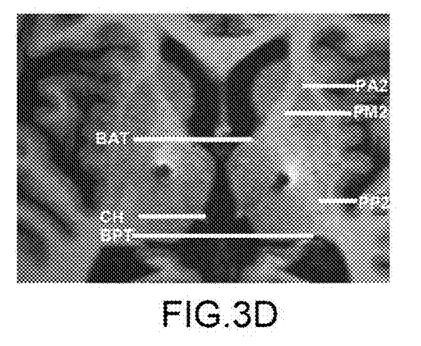
Figure 3E:
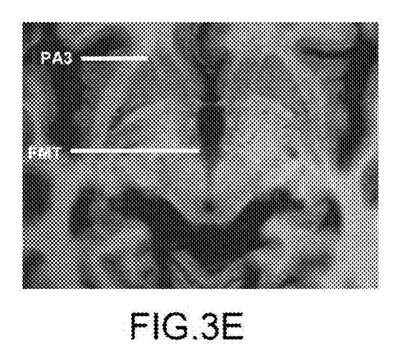
Figure 3F:
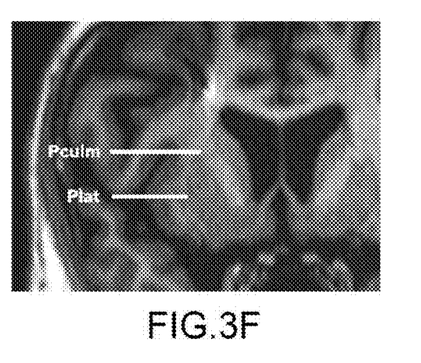

FIGS. 3A to 3F show MRI images viewed along various sections. FIG. 3A is an axial section (axial reference plane). FIG. 3B is a sagittal section, along the sagittal plane defined above. FIG. 3C is an axial section (first axial plane). FIG. 3D is an axial section (second axial plane). FIG. 3E is an axial section (third axial plane). FIG. 3F is a coronal section, along the coronal plane defined above.

Other marker points may be used depending on the planned neurosurgical intervention. Thus, since the target points depend on the pathology to be treated, in general, marker points may be chosen that are able to be correlated with said target points and are easily identifiable in conventional imaging, such as MRI.

According to the particular embodiment, the marker points PR may be represented in a matrix X where $X \in \mathbb{R}^{m \times 3}$, m representing the number of marker points, m×3 representing all of the coordinates of all of these marker points.

Each row of the matrix X represents a given marker point. Each column represents one of the three coordinates.

By concatenating the coordinates of the marker points, the matrix X may be reshaped into a vector $X \in \mathbb{R}^{3 \times m}$. Throughout the rest of the description, such a vector X will be considered, which comprises a plurality (3×m) of scalar elements.

Each of the 18 marker points is characterized by its three coordinates $x_{PR}$, $y_{PR}$, $z_{PR}$ in the mathematical coordinate system used. That makes a total of 54 coordinates.

In general, determination is performed by hemisphere: right hemisphere (denoted by "HD" in the present description) and left hemisphere (denoted by "HG" in the present description). There are then 18 points, or 54 coordinates in the HD and 18 points, or 54 coordinates in the HG. In this case, m=36 and a total of 108 coordinates are obtained.

Thus, it is possible either to construct one prediction function FG for the left hemisphere, which makes it possible to determine the left-hand target, and another prediction function FD for the right hemisphere which makes it possible to determine the right-hand target, or to construct a single function F which makes it possible to determine both targets (the right-hand target and the left-hand target).

Tartlet Points (or Stimulation Points)

The target (grouping together the one or more target points PC) is represented in a vector Y where $Y \in \mathbb{R}^p$. A vector Y comprises a plurality (p) of scalar elements.

The number of target points in a target is variable. The value p depends on the number of target points multiplied by the number of coordinates per point. The coordinates may be Cartesian coordinates $x_{PC}$, $y_{PC}$, $z_{PC}$ of the target point.

In the case of deep brain stimulation, the coordinates may further comprise coordinates characterizing the direction of the stimulation electrode at this point. By knowing a stimulation point and the direction of the electrode at this point, it is possible to find other stimulation points on the same electrode. The stimulation points are also called "stimulation zones". Each electrode E1, E2 may, for example, have four zones, as shown for example in FIG. 2. Point 0 may represent a target point PC1, PC2. Patients may thus be stimulated via one or two zones per hemisphere. In the example of FIG. 2, zones 0 and 1 are entirely in the target, zone 2 is partially in and zone 3 is not in the target. For example, each zone is 1.5 mm long and two zones are spaced 0.5 mm apart.

If only the coordinates for a target point are sought, then p=3 corresponding to the three coordinates $x_{PC}$, $y_{PC}$, $z_{PC}$ of the target point in the mathematical coordinate system used.

If, in the case of deep brain stimulation, the direction of the electrode for a stimulation point is also sought, then p=6 corresponding to the target $x_{PC}$, $y_{PC}$, $z_{PC}$ plus the coordinates of the direction vector of the electrode $V_{xPC}$, $V_{yPC}$, $V_{zPC}$ along the three axes of the mathematical coordinate system used.

Other coordinates may be added depending on the planned neurosurgical intervention. For example, for Gamma Knife or focused ultrasound treatment, the coordinates of the target points may be adapted.

If it is desired to establish the coordinates of a target point on the one hand for the right hemisphere, and on the other hand for the left hemisphere, then p=6 (only Cartesian coordinates) or p=12 (including the vector coordinates).

Since there may therefore be one or more target points (or zones) in a target, the value p is equal to the number of points multiplied by the coordinates used for each point.

Learning Database

For a patient i (i=1 . . . n), there is a vector $X_i$ (of 3×m values $x_i$) of marker points and a vector $Y_i$ (of p values $y_i$) of target points. The vectors $(X_i, Y_i)_{i=1 \ldots n}$ extracted from n patients define the entirety of the learning database.

Learning Step (Constructing a Function Y=F(X))

Using a supervised statistical learning method, the method according to the invention constructs a prediction function F such that Y≈F(X).

The prediction function may be called simply "function" in the present description.

The function F takes as argument X or a part of X to produce Y.

For a new patient for whom the target has to be determined, the vector X' of the marker points then has to be determined from MRI, for example preoperative MRI performed before surgery.

The position Y' of the target is then determined using the function F as follows:

$$\tilde{Y}'=F(\tilde{X}')$$

$\tilde{Y}'$ is the value obtained for the position Y' of the target by means of the method according to the invention.

According to one particular embodiment, the supervised statistical learning method comprises the use of the kernel ridge regression method in a reproducing kernel Hilbert space.

The following description describes this particular embodiment.

Kernel ridge regression is a relatively simple method. It generally uses the entirety of the learning database and is suitable for "small" learning databases (number of patients (n) smaller than 20) or "medium" databases (number of patients (n) between 20 and 100).

The function F is sought in a Hilbert space $(\mathcal{H}, \langle .,. \rangle_{\mathcal{H}})$ using the method of least squares with a regularization term $\lambda \|F\|_{\mathcal{H}}$ where $\lambda$ is a regularization coefficient. Regularization ensures that the norm $$\|F\|_{\mathcal{H}} = \langle F, F \rangle_{\mathcal{H}}^{\frac{1}{2}}$$

and therefore the function F does not degenerate.

Thus, the chosen Hilbert space $\mathcal{H}$ is a reproducing kernel Hilbert space based on a Gaussian kernel:

$$K(x, y) = e^{-\frac{|x-y|^2}{2\sigma^2}}, \forall x, y \in \mathbb{R}^{3 \times m}$$

The kernel is said to be "reproducing" in the space $\mathcal{H}$ by the property given by the following equation (1):

$$F(x) = \langle F(.), K(.,x) \rangle_{\mathcal{H}}$$

$$F \in \mathcal{H}, \forall x \in \mathbb{R}^{3 \times m} \quad (1)$$

where $\langle .,. \rangle_{\mathcal{H}}$ is the scalar product in $\mathcal{H}$.

The following regularized least squares problem is considered in the Hilbert space $\mathcal{H}$: given a learning database $\{(X_i, y_i)\}_{i=1}^{n} \in (\mathbb{R}^{3 \times m} \times \mathbb{R})^n$ where n is the number of elements in the database, the objective is to solve the following equation (2):

$$\min_{f \in \mathcal{H}} \left\{ \frac{1}{n} \sum_{i=1}^{n} (F(X_i) - y_i)^2 + \lambda \|F\|_{\mathcal{H}}^2 \right\} \quad (2)$$

where $\lambda > 0$ is the given regularization coefficient.

Riesz representation theorem indicates that the solution to equation (2) may be written as:

$$F(x) = \sum_{i=1}^{n} \alpha_i K(x, X_i)$$

where $\alpha = (\alpha_i)_{i=1 \ldots n} \in \mathbb{R}^n$ is a new unknown.

By defining the Gram matrix $K=(K_{ij})_{i,j=1 \ldots n}$ with $K_{ij}=K(x_i, x_j)$, equation (2) to be solved is equivalent to solving the following equation (3):

$$\min_{\alpha \in \mathbb{R}^n} \left\{ \frac{1}{n}(K\alpha - y)^T (K\alpha - y) + \lambda \alpha^T K \alpha \right\} \quad (3)$$

the solution of which is given simply by equation (4):

$$\alpha = (K + \lambda n I)^{-1} y \quad (4)$$

I being the identity matrix in $\mathbb{R}^n$.

Since the target (grouping together the one or more target points) is not defined by just a scalar characteristic but by a Y vector of size p containing the coordinates of each target point and/or the direction of a stimulation electrode to be positioned at each point (characterized by the coordinates of a vector in the three axes) and/or other coordinates depending on the planned neurosurgical intervention, it is a matter of solving the following equation (5):

$$A = (K + \lambda n I)^{-1} Y \quad (5)$$

I being the identity matrix in $\mathbb{R}^n$.

$A \in \mathbb{R}^{n \times p}$ and $Y \in \mathbb{R}^{n \times p}$.

Each column of A corresponds to the coefficient α for a given coordinate of the target (between 1 and p). Each column of Y corresponds to the values of a given coordinate of the target (between 1 and p).

Knowing that, as indicated above, K is the Gaussian kernel defined by the Gram matrix:

$$K = (K_{i,j})_{i,j=1...n} = K(x_i, x_j) = e^{-\frac{|(x_i)-(x_j)|^2}{2\sigma^2}} \quad (6)$$

Reconstruction Step (New Patient)

Once the learning step has ended, i.e. the function F has been constructed, it is possible to reconstruct a target, i.e. to determine the vector $\tilde{Y}'$ of the coordinates of the one or more target points on the basis of a set of marker points $\tilde{X}' \in \mathbb{R}^{3 \times m}$ determined for example from the MRI of a patient, using the following equation (7):

$$\tilde{Y}' = \tilde{K}A \quad (7)$$

where $$\tilde{K}_j = K(\tilde{X}'; x_j), j = 1 \ldots n$$

In the case of adding functional data to the database, the following notations are introduced.

At least one vector $X_i$ takes into account all of the preoperative anatomical data such as the 18 marker points, but also functional data such as the evaluation scores for the symptoms of the pathology. The size of the vector $X_i$ will therefore be 3×m+M, where M is the number of functional data, for example parameters resulting from the evaluation of the patient's preoperative symptoms (or "preoperative scores").

For each patient i in the database, a vector postOpVector$_i$ is defined. This vector may contain, for example, parameters resulting from the evaluation of postoperative symptoms (or "postoperative scores"), and/or electrical parameters (frequency, amplitude and duration) of stimulation.

The function to be minimized when taking the functional data into account is:

$$\min_{f \in \mathcal{H}} \left\{ \frac{1}{n} \sum_{i=1}^{n} (F(X_i) - y_i)^2 W(\text{postOpVector}_i) + \lambda \|F\|_{\mathcal{H}}^2 \right\} \quad (8)$$

where W is the weight function and measures the confidence in a patient's data. This weight function may be chosen to be complex or simple. One example of the weight function is the inverse of the stimulation amplitude or the inverse of the amount of current injected per second, which corresponds to the inverse of the product of the stimulation parameters.

In this latter case:

$$W(\text{postOpVector}_i) = \frac{1}{\text{frequency} * \text{duration} * \text{amplitude}} \quad (9)$$

Another example of a weight function is the inverse of the sum of the patient's postoperative scores which reflects the fact that the lower the score, the better placed the electrode.

The weight function W may also take another expression combining the postoperative scores and the electrical parameters.

Selection Step

The function obtained by solving equation (5) does not include any selection of marker points or coordinates of these points, in the sense that the 54 coordinates of the 18 marker points extracted from the MRI (or the 108 coordinates of the 36 points if both hemispheres of the brain are taken into account) are used in the learning and reconstruction steps. However, some coordinates are not correlated with the target. This compromises the accuracy in determining the target.

Preferably, the method comprises a selection step in order to use only the coordinates of the marker points which are correlated with the target.

The selection step may comprise the use of a projection operator $\pi \in \Pi(\mathbb{R}^{3 \times m})$ where $\Pi(\mathbb{R}^{3 \times m})$ is the set of all of projectors in $\mathbb{R}^{3 \times m}$.

The selection of the coordinates of the optimal marker points combined with the construction of the prediction function F is made possible by solving the following equation (10):

$$\min_{F \in \mathcal{H}, \pi \in \prod(\mathbb{R}^{3 \times m})} \left\{ \frac{1}{n} \sum_{i=1}^{n} (F(\pi(X_i)) - y_i)^2 + \lambda \|F \circ \pi\|_{\mathcal{H}}^2 \right\} \quad (10)$$

The selection corresponds to the optimization of the projection operator π. In practice, this is done by calculating the sensitivity of the function to be minimized to each of the characteristics (coordinates of the marker points) considered.

This allows the accuracy in determining the target to be improved.

Parameter Optimization Step

The method comprises the construction of a function F dependent on a relatively small number of parameters which have to be optimized in order to obtain the most accurate function possible, and thus in order to obtain the most accurate (and therefore the most effective) target: the regularization coefficient Λ, the width of the Gaussian kernel σ, and the projection operator π.

The optimization of these parameters is solved iteratively.

The parameters Δ, σ and π are optimized using a "cross-validation" procedure of "leave-one-out" type.

The principle of cross-validation of "leave-one-out" type is to construct a prediction function with all of the examples (here the patients) in a learning database except one (patient) and to evaluate the performance of the constructed function on the example removed from the learning database. The procedure is reproduced by reproducing this procedure for each of the patients of the entirety of the learning database.

According to one embodiment, the "leave-one-out cross-validation error" (also called "LOOE") is used for the set values of σ, Δ and the operator π, which is obtained as follows by formula (11) below:

$$LOOE(\sigma, \lambda, \pi) = \sum_{i=1}^{n} \frac{\|y_i - \tilde{\tilde{Y}}_i\|^2}{(1 - S(i,i))^2} \quad (11)$$

where $S = K(K + \lambda I)^{-1}$ and $\tilde{\tilde{Y}} = Sy$.

The matrix K integrates the projection operator π since:

$$K=(K_{ij})_{i,j=1...n} \text{ with } K_{ij}=k(\pi(X_i),\pi(X_j)).$$

According to a first variant, the two parameters σ and λ and the operator π are optimized directly using an algorithm for global optimization by evolution strategy. This algorithm is based on the CMA-ES (abbreviation of "covariance matrix adaptation-evolution strategy") method; it makes it possible to solve equation (12) below:

$$(\sigma, \lambda, \pi) = \underset{\sigma \in R, \lambda \in R, \pi \in \prod(R^{3 \times m})}{\operatorname{argmin}} LOOE(\sigma, \lambda, \pi) \quad (13)$$

According to this first variant, the method comprises the following steps corresponding to direct optimization:
Step 1: constructing/initializing the learning database
    Loading the data
    Defining the input data (marker points PR) $(X_i)_{i-1}^n$
    Defining the output data (target points PC) $(Y_i)_{i=1}^n$
    Constructing a preliminary function F, $F_P$
Step 2: optimizing the parameters
    Solving equation (12)
Step 3: Constructing the consolidated function Fc with the optimal parameters λ, σ and π (π integrating the optimal coordinates of the marker points PR)
Step 4: reconstructing for a new patient:
    Performing preoperative MRI (for example 1.5 T MRI)
    Determining the 18 marker points PR' visible in the MRI
    Determining target points PC' (target) using the consolidated function Fc and the marker points PR'.

According to this first variant, the selection step and the optimization step are carried out at the same time, the selection being made by optimizing the projection operator π.

The problem of this first variant embodiment is the size of the projection operator π which is 18×3=54, or 18×3×2=108 in the case where both hemispheres are combined for the reconstruction of the target. In this case, the number of parameters to be optimized is too large in the sense that the number of possibilities for the operator π is $2^{54}$ or $2^{108}$ depending on the size of the operator in addition to the two parameters λ and σ.

Figure 5:
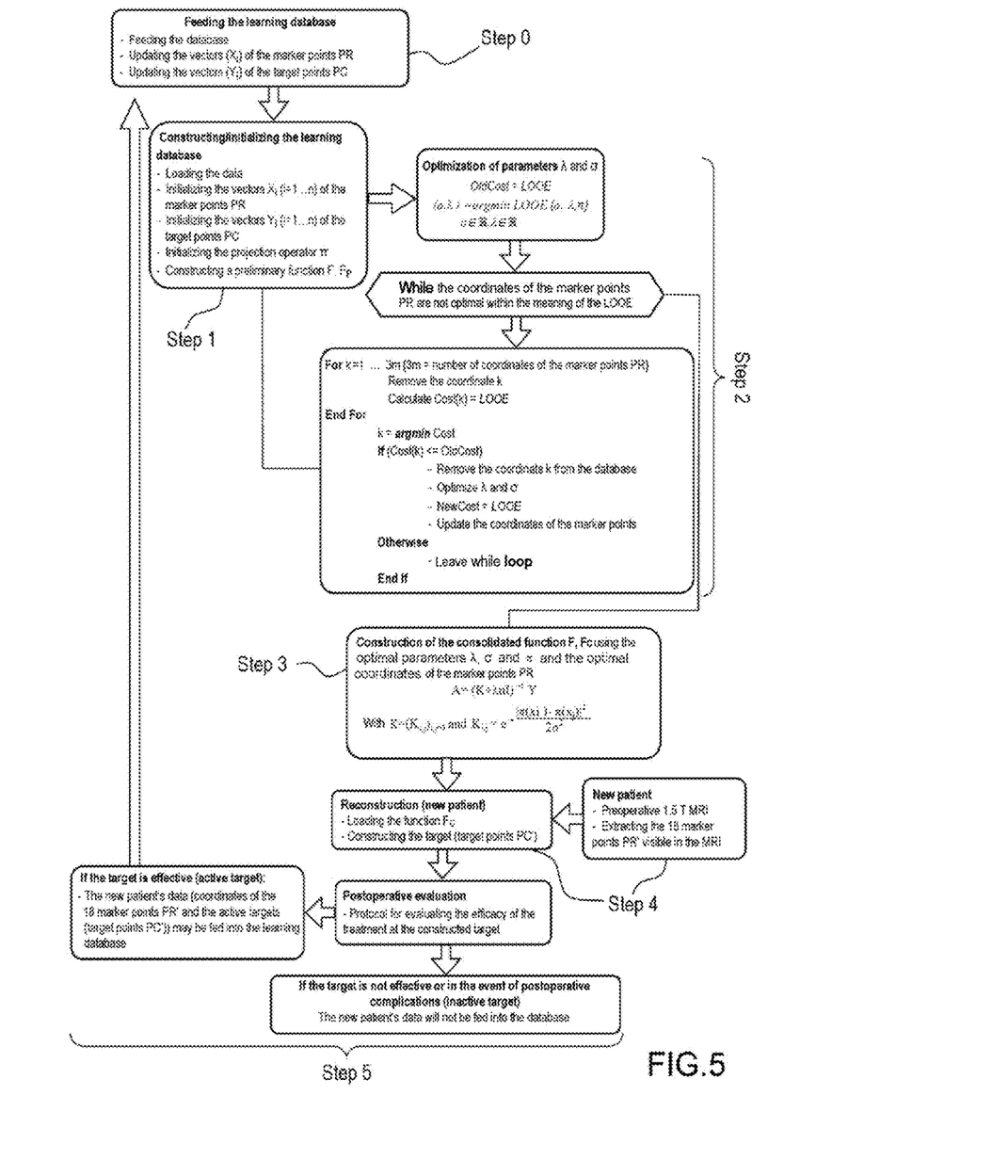
FIG. 5 is a flowchart showing an exemplary method according to the invention, as well as variants.

According to a second variant described in particular with reference to FIG. 5, the two parameters σ and λ and the operator π are optimized indirectly. An iterative method able to optimize both the parameters λ and σ and the projection operator π is used.

First, the following equation (13) is solved:

$$(\sigma, \lambda) = \underset{\sigma \in R, \lambda \in R}{\operatorname{argmin}} LOOE(\sigma, \lambda, \pi) \quad (13)$$

Next, the sensitivity of the LOOE function to the removal of one of the coordinates (k) of the marker points is tested. When a $k^{th}$ coordinate is removed, two possible results are obtained and processed:
    if the LOOE increases, it means that the target points and the $k^{th}$ coordinate are correlated and this coordinate has to be retained;
    if the LOOE stays constant or decreases, it means that the target points and the $k^{th}$ coordinate are not correlated and that this $k^{th}$ coordinate may potentially be removed.

Among the potentially removable coordinates, the one which is least correlated with the targets is removed.

Each time a coordinate is removed, the projection operator π is updated (with one fewer coordinate) and the parameters σ and λ are optimized using the LOOE function.

This procedure is repeated until no coordinates have to be removed. In this case, all of the remaining coordinates are necessary in order to retain an optimal solution within the meaning of the LOOE.

According to this second variant, the method comprises the following steps, corresponding to indirect optimization:
Step 1: constructing/initializing the learning database
    Loading the data
    Defining the input data (marker points PR) $(X_i)_{i-1}^n$
    Defining the output data (target points PC) $(Y_i)_{i=1}^n$
    Initializing the projection operator π
    Constructing a preliminary function F, $F_P$ assuming π to be equal to the identity function
Step 2: optimizing the parameters
    Performing a first optimization of σ and λ with equation (13)
    Performing the loop operation: While the coordinates present in the operator π are not optimal (within the meaning of the LOOE):
        For each coordinate k (k=1 to 3×m) of the marker points:
            performing the calculation of the LOOE without the coordinate k;
            if the LOOE stays constant or decreases, then it is noted that the coordinate k of the learning database is potentially removable;
            otherwise the coordinate k is retained and the next coordinate k+1 is considered;
        removing the coordinate $k_{min}$ from among the potentially removable coordinates; the coordinate $k_{min}$ being that which is the least correlated with the targets within the meaning of the LOOE, in other words that which, if it is taken into account, degrades the LOOE the most;
        updating the operator π without the coordinate $k_{min}$ and redoing optimization of σ and λ with equation (13).
    End of the while loop.
Step 3: Constructing the consolidated function Fc with the optimal parameters λ, σ and the operator π (integrating the optimal coordinates of the marker points PR)
Step 4: reconstructing for a new patient
    Performing preoperative MRI (for example 1.5 T MRI)
    Determining the 18 marker points PR' visible in the MRI
    Determining target points PC' (target) using the consolidated function Fc and the marker points PR'.

As illustrated in FIG. 5, other steps may be added to the method:
    a step 5 of evaluating the efficacy of the stimulation (more broadly of the neurosurgical treatment) carried out at the target determined according to the method: this step is carried out in the months following the treatment. It is, for example, possible to use the UPDRS-3 scale for Parkinson's disease (STN and GPi targets) and the Fahn-Tolosa-Marin scale for essential tremor (VIM target);
    a step 0 of feeding the learning database: specifically, the database may be fed using new cases of patients for whom the clinical outcome has been deemed optimal according to the postoperative evaluation (for whom the target was determined by the method according to the invention or otherwise).

Step 5 and/or step 0 make it possible to enrich the learning database with data from new patients for whom the treatment has been evaluated as effective.

Other supervised statistical learning methods may be used, for example a method of support-vector machine (SVM) type which does not use the entire learning database but only a subset (the support vectors), unlike kernel ridge regression. The use of such a method is possible when the learning database is "large", i.e. when the number of patients (n) in the database is greater than or equal to 100. In this case, it makes it possible to have a less expensive method.

It is also possible to use a method of neural network type when the learning database is large.

Advantageously, when the learning database is enriched with data from new patients until the critical size of 100 patients is reached, a method of support-vector machine or neural network type may be used as the supervised statistical learning method to construct the function F(X)=Y.

Advantageously, it is also possible to introduce a step of statistical classification (whether supervised or unsupervised) in order to define a plurality of classes in the learning database, each class containing a subset of patient data (according, for example, to pathology, age, other diseases, etc.) distinct from the data of another class. Next, for each of the classes, a metamodel, i.e. a prediction function F, is constructed, for example as described in the second variant with reference to FIG. 5.

Statistical classification (whether supervised or unsupervised) may also be implemented according to the coordinates of the marker points of the various patients in the database. In the latter case, the classes may group together patients with similar coordinates, so that their targets may also be similar.

To construct the target for a given new patient, all that has to be done is to identify to which class the new patient belongs and to use the function F corresponding to this class to predict the target. This may allow targeting accuracy to be improved.

The statistical classification may be performed using one of the following methods:
  logistic regression
  SVM
  hierarchical classification method
  neural networks
  random forests Any other suitable statistical classification method may be used.

The various embodiments presented may be combined with one another.

All or some of the following steps: step of constructing and/or initializing the learning database, learning step, selection step, parameter optimization step, reconstruction step, defining the mathematical coordinate system and/or the marker points described in the embodiment may be used for any application of the method other than deep surgical stimulation, generally in preparation for any neurosurgical treatment requiring at least one precise brain target to be determined.

In addition, the present invention is not limited to the embodiments described above but rather extends to any embodiment that comes within the scope of the claims.

The method, system and computer program according to the invention may find applications other than preparation for deep brain stimulation. The invention may be used in a preparation step for a treatment of "Gamma Knife" type in order to determine the area for the application of the ionizing beam. It may also be used in a preparation step for a high-intensity focused ultrasound (HIFU) treatment in order to determine the area for the application of the ultrasound beam.

In general, the invention may find application in the preparation for any neurosurgical treatment requiring at least one brain target to be determined.

The invention claimed is:

1. A method for determining a stereotactic brain target comprising at least one target point (PC), said method being implemented on a processor prior to neurosurgical treatment at said target for a given pathology and comprising the following steps:
  selecting a plurality (n) of clinical cases of patients for whom a measured result is greater than or equal to a threshold, following said treatment performed for said pathology at the at least one target point (PC), postoperative imaging having been performed for each of said patients;
  selecting a mathematical coordinate system;
  processing said postoperative imaging so as to determine, for each selected clinical case, all or some of (p) coordinates ($x_{PC}$, $y_{PC}$, $z_{PC}$, $v_{xPC}$, $v_{yPC}$, $v_{zPC}$) of the at least one target point (PC) in the selected coordinate system;
  selecting a plurality (m) of brain marker points (PR);
  processing the postoperative imaging so as to determine, for each selected clinical case, all or some of (3×m) coordinates ($x_{PR}$, $y_{PR}$, $z_{PR}$) of the brain marker points (PR);
  creating a learning database comprising determined coordinates of one or more of the at least one target point (PC) and determined coordinates of the marker points (PR) of all of the (n) selected clinical cases;
  determining a prediction function (F) giving the coordinates of said at least one target point (PC) according to the marker points (PR) by using the learning database and a supervised statistical learning method;
  processing preoperative imaging of a new patient to be treated for said pathology so as to determine all or some of coordinates ($x_{PR'}$, $y_{PR'}$, $z_{PR'}$) of marker points (PR') of said new patient; and
  using the prediction function (F) so as to obtain the coordinates of said at least one target point (PC) for said new patient according to the coordinates of the marker points (PR) determined for said new patient.

2. The method as claimed in claim 1, further comprising a step of:
  consolidating the prediction function (F) using a cross-validation method, said consolidating step resulting in a consolidated prediction function ($F_C$) giving the coordinates of the at least one target point (PC) according to the marker points (PR);
  the step of using the prediction function (F) consisting in using the consolidated prediction function ($F_C$).

3. The method as claimed in claim 1, the imaging processed to determine coordinates of the marker points (PR, PR') and/or of the at least one target point (PC) being at least one MRI image.

4. The method as claimed in claim 1, the supervised statistical learning method comprising using a kernel ridge regression method in a reproducing kernel Hilbert space.

5. The method as claimed in claim 1, the supervised statistical learning method comprising using a method of support-vector machine type.

6. The method as claimed in claim 1, the supervised statistical learning method comprising using a method of neural network type.

7. The method as claimed in claim 2, the cross-validation method comprising using a leave-one-out cross-validation method.

8. The method as claimed in claim 2, the cross-validation method comprising using a leave-k-out cross-validation method.

9. The method as claimed in claim 1, the mathematical coordinate system being an orthonormal Cartesian coordinate system, a first straight line (CACP) passing through a superior and a posterior edge of the anterior commissure (CA) and an inferior and an anterior edge of the posterior commissure (CP) forming an Oy axis, the inferior and anterior edge of the posterior commissure (CP) forming a center of the coordinate system, and an Oz axis being a second straight line perpendicular to the first straight line (CACP) in an interhemispheric plane.

10. The method as claimed in claim 1, the marker points (PR) being chosen from among the following eighteen points:
- a first marker point (FMT) being the mamillothalamic fasciculus on the third axial plane;
- second, third and fourth marker points (PA1, PA2, PA3) being an anterior point of the putamen on each of first, second and third axial planes;
- fifth and sixth marker points (PM1, PM2) being a medial point of the putamen on the first and second axial planes;
- seventh and eighth marker points (PP1, PP2) being a posterior point of the putamen on the first and second axial planes;
- a ninth marker point (CH) being the habenular commissure on the second axial plane;
- a tenth marker point (BAT) being an anterior edge of the thalamus on the second axial plane;
- an eleventh marker point (BPT) being a posterior edge of the thalamus on the second axial plane;
- a twelfth marker point (CA) being the anterior commissure;
- a thirteenth marker point (A) being a medial edge of the third ventricle at a mid-commissural point;
- a fourteenth marker point (B) being a height of the thalamus on a sagittal plane passing through the thirteenth marker point (A);
- a fifteenth marker point (C) being a midpoint of a segment [AB] defined by the thirteenth and fourteenth marker points;
- a sixteenth marker point (D) being the anterior edge of the thalamus on a straight line parallel to another straight line (CACP) passing through a superior and a posterior edge of the anterior commissure and an inferior and an anterior edge of the posterior commissure and passing through the fifteenth marker point (C);
- a seventeenth marker point ($P_{culm}$) being a superior edge of the putamen on a coronal plane passing through the fifth marker point (PM1); and
- an eighteenth marker point ($P_{lat}$) being a lateral edge of the putamen on the coronal plane passing through the fifth marker point (PM1).

11. The method as claimed in claim 1, further comprising an additional step of adding functional data to the learning database, said functional data being able to add at least one indicator of a degree of confidence in target points (PC) and marker points (PR) of the clinical cases.

12. The method as claimed in claim 1, implemented on a processor prior to deep brain stimulation, Gamma Knife, or focused ultrasound treatment.

13. A data processing system comprising a processor configured to implement all or some of the steps of the method as claimed in claim 1.

14. A non-transitory computer-readable storage medium on which is stored a computer program comprising instructions which, when the program is executed by a processor, to implement the method as claimed in claim 1.

* * * * *